(12) United States Patent
Bang et al.

(10) Patent No.: US 11,733,227 B2
(45) Date of Patent: Aug. 22, 2023

(54) METHOD AND SYSTEM FOR DETECTING A FALSE ALARM EVENT IN GAS DETECTION

(71) Applicant: Honeywell International Inc., Charlotte, NC (US)

(72) Inventors: KiHo Bang, Seoul (KR); JePhil Ahn, Seoul (KR); Dongil Ko, Seoul (KR); ByungYong Lee, Seoul (KR); Chikang Lee, Seoul (KR)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 367 days.

(21) Appl. No.: 17/074,885

(22) Filed: Oct. 20, 2020

(65) Prior Publication Data

US 2021/0132015 A1  May 6, 2021

(30) Foreign Application Priority Data

Nov. 4, 2019  (KR) .................. 10-2019-0139479

(51) Int. Cl.
  *G01N 33/00* (2006.01)
  *G01M 3/04* (2006.01)
  *G01L 11/00* (2006.01)

(52) U.S. Cl.
  CPC ............ *G01N 33/007* (2013.01); *G01L 11/00* (2013.01); *G01M 3/04* (2013.01)

(58) Field of Classification Search
  CPC .......... G01M 3/26; G01M 3/20; G01M 3/226; G01M 3/3236; G01M 3/02
  (Continued)

(56) References Cited

U.S. PATENT DOCUMENTS 5,049,168 A * 9/1991 Danielson ............. G01M 3/202
  417/244
5,293,771 A * 3/1994 Ridenour ................ G01M 3/20
  73/40

(Continued)

FOREIGN PATENT DOCUMENTS

CN  101375158 A  2/2009
CN  202317232 U  7/2012
(Continued)

OTHER PUBLICATIONS

ESPACENET Machine Translation of CN 208497692 U Which Originally Published on Feb. 15, 2019. (Year: 2019).*

(Continued)

*Primary Examiner* — David A. Rogers
(74) *Attorney, Agent, or Firm* — Alston & Bird LLP

(57) ABSTRACT

A gas-detecting apparatus, having a gas inlet and a gas outlet, for detecting a false alarm is disclosed. The gas-detecting apparatus comprises a control module, a sensor module, and an air chamber. In an example embodiment, the sensor module is electrically connected with the control module. The sensor module has a sensor inlet and a sensor outlet. The sensor inlet is fluidly coupled to the gas inlet of the gas-detecting apparatus. The air chamber has an air inlet and an air outlet, wherein the air inlet is fluidly coupled to the gas inlet of the gas-detecting apparatus and the air outlet is fluidly coupled to the gas outlet. The control module is configured to receive a first sensing signal for a first level of gas from the sensor module and determine whether magnitude of the first sensing signal is higher than a first threshold value. In an instance when the magnitude of the first sensing signal is higher than the first threshold value, the control module causes the air chamber to supply ambient air to the sensor module through the sensor inlet of the sensor module.

20 Claims, 12 Drawing Sheets

(58) Field of Classification Search
USPC .................................................. 73/40–49.8
See application file for complete search history.

(56) References Cited

U.S. PATENT DOCUMENTS

| | | | | |
|---|---|---|---|---|
| 7,165,443 | B2 * | 1/2007 | Chin | G01M 3/226 |
| | | | | 73/40.7 |
| 7,472,581 | B2 * | 1/2009 | Kitazawa | G01M 3/3236 |
| | | | | 73/49.2 |
| 7,641,382 | B2 * | 1/2010 | Izawa | C23C 16/4401 |
| | | | | 374/45 |
| 7,805,974 | B2 * | 10/2010 | Scheffler | G01N 33/007 |
| | | | | 73/1.06 |
| 7,879,137 | B2 * | 2/2011 | Parekh | G03F 7/70933 |
| | | | | 95/52 |
| 7,955,797 | B2 * | 6/2011 | McManus | G06Q 10/087 |
| | | | | 422/62 |
| 8,393,197 | B2 * | 3/2013 | Monkowski | G01M 3/202 |
| | | | | 73/40.7 |
| 8,815,616 | B2 * | 8/2014 | Bang | F16K 51/02 |
| | | | | 414/217 |
| 9,170,246 | B2 * | 10/2015 | Dietz | H01L 22/10 |
| 9,176,021 | B2 * | 11/2015 | Patel | G01M 3/20 |
| 9,322,098 | B2 * | 4/2016 | Grange | G01M 3/20 |
| 9,677,976 | B2 * | 6/2017 | Chrin, II | G01N 33/0062 |
| 9,945,826 | B2 * | 4/2018 | Oberlin | G01N 25/18 |
| 10,724,418 | B2 * | 7/2020 | Karpe | F01N 9/002 |
| 11,137,273 | B2 * | 10/2021 | Zhou | G01D 11/245 |
| 11,255,833 | B2 * | 2/2022 | Hur | G01N 33/0063 |
| 2006/0108221 | A1 * | 5/2006 | Goodwin | G01N 33/0009 |
| | | | | 204/424 |
| 2020/0386732 | A1 | 12/2020 | Park et al. | |

FOREIGN PATENT DOCUMENTS

| | | | |
|---|---|---|---|
| CN | 208497692 U | * | 2/2019 |
| CN | 111566794 A | | 8/2020 |
| WO | 2019/139183 A1 | | 7/2019 |

OTHER PUBLICATIONS

CN Office Action dated Oct. 10, 2022 for CN Application No. 202011156242.

CN Search report dated Oct. 10, 2022 for CN Application No. 202011156242.

English Translation of CN Office Action dated Oct. 10, 2022 for CN Application No. 202011156242.

CN Office Action dated Mar. 10, 2023 for CN Application No. 202011156242, 8 page(s).

English Translation of CN Office Action dated Mar. 10, 2023 for CN Application No. 202011156242, 4 page(s).

* cited by examiner

METHOD AND SYSTEM FOR DETECTING A FALSE ALARM EVENT IN GAS DETECTION

TECHNOLOGICAL FIELD

Exemplary embodiments of the present disclosure relate generally to gas detection and, more particularly, to methods and systems for detecting a false alarm event in gas detection.

BACKGROUND

Various gases are used in semiconductor processing lines and in industrial sites, and gas-detecting apparatuses are commonly used to prevent large scale accidents caused by gas leaks. Such a gas-detecting apparatus may detect a gas leaked from a chamber in which a semiconductor process is performed, or a gas pipe or valve connected to the chamber, or may determine whether or not a gas leak has occurred in an industrial site. When such a gas-detecting apparatus detects a gas leak and sounds an alarm, a gas pipe connected to the chamber is shut off or operations of the chamber are stopped. Therefore, it is important that the gas-detecting apparatus accurately determines whether a gas leak has occurred.

Applicant has identified a number of deficiencies and problems associated with conventional techniques of detecting gas for false alarm detection. Through applied effort, ingenuity, and innovation, many of these identified problems have been solved by developing solutions that are included in embodiments of the present disclosure, many examples of which are described in detail herein.

BRIEF SUMMARY

According to the embodiments disclosed herein, a gas-detecting apparatus, having a gas inlet and a gas outlet, for detecting a false alarm is disclosed. The gas-detecting apparatus comprises a control module, a sensor module, and an air chamber. In an example embodiment, the sensor module is electrically connected with the control module. The sensor module has a sensor inlet and a sensor outlet. The sensor inlet is fluidly coupled to the gas inlet of the gas-detecting apparatus. The air chamber has an air inlet and an air outlet, wherein the air inlet is fluidly coupled to the gas inlet of the gas-detecting apparatus and the air outlet is fluidly coupled to the gas outlet. The control module is configured to receive a first sensing signal for a first level of gas from the sensor module and determine whether a magnitude of the first sensing signal is higher than a first threshold value. In an instance when the magnitude of the first sensing signal is higher than the first threshold value, the control module causes the air chamber to supply ambient air to the sensor module through the sensor inlet of the sensor module.

According to the embodiments disclosed herein, the gas-detecting apparatus having the gas inlet and the gas outlet is disclosed. The gas-detecting apparatus comprises the control module, the sensor module, a valve, the air chamber, a pump, and a solenoid valve. In an example embodiment, the sensor module is electrically connected with the control module and has the sensor inlet and the sensor outlet. The sensor outlet is fluidly coupled to the gas inlet of the gas-detecting apparatus. The valve is electrically connected with the control module and has a valve inlet and a valve outlet. In an example embodiment, the valve outlet is fluidly coupled to the sensor inlet of the sensor module. In an example embodiment, the air chamber has the air inlet and the air outlet. In an example embodiment, the air inlet is fluidly coupled to the gas inlet of the gas-detecting apparatus, the air outlet is fluidly coupled to the gas outlet, and the valve inlet is fluidly coupled to the air inlet of the air chamber. The pump is electrically connected with the control module, wherein the pump has a pump inlet and a pump outlet. The solenoid valve is electrically connected with the control module, the solenoid valve having an inlet, a first outlet, and a second outlet, wherein the inlet of the solenoid valve is fluidly coupled to the pump outlet, and the second outlet is fluidly coupled to the air inlet of the air chamber. In an example embodiment, the control module is configured to receive a first sensing signal for a first level of gas from the sensor module and determine whether a magnitude of the first sensing signal is higher than a first threshold value. The control module then causes the air chamber to supply ambient air to the sensor inlet of the sensor module, when the magnitude of the first sensing signal is higher than the first threshold value.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
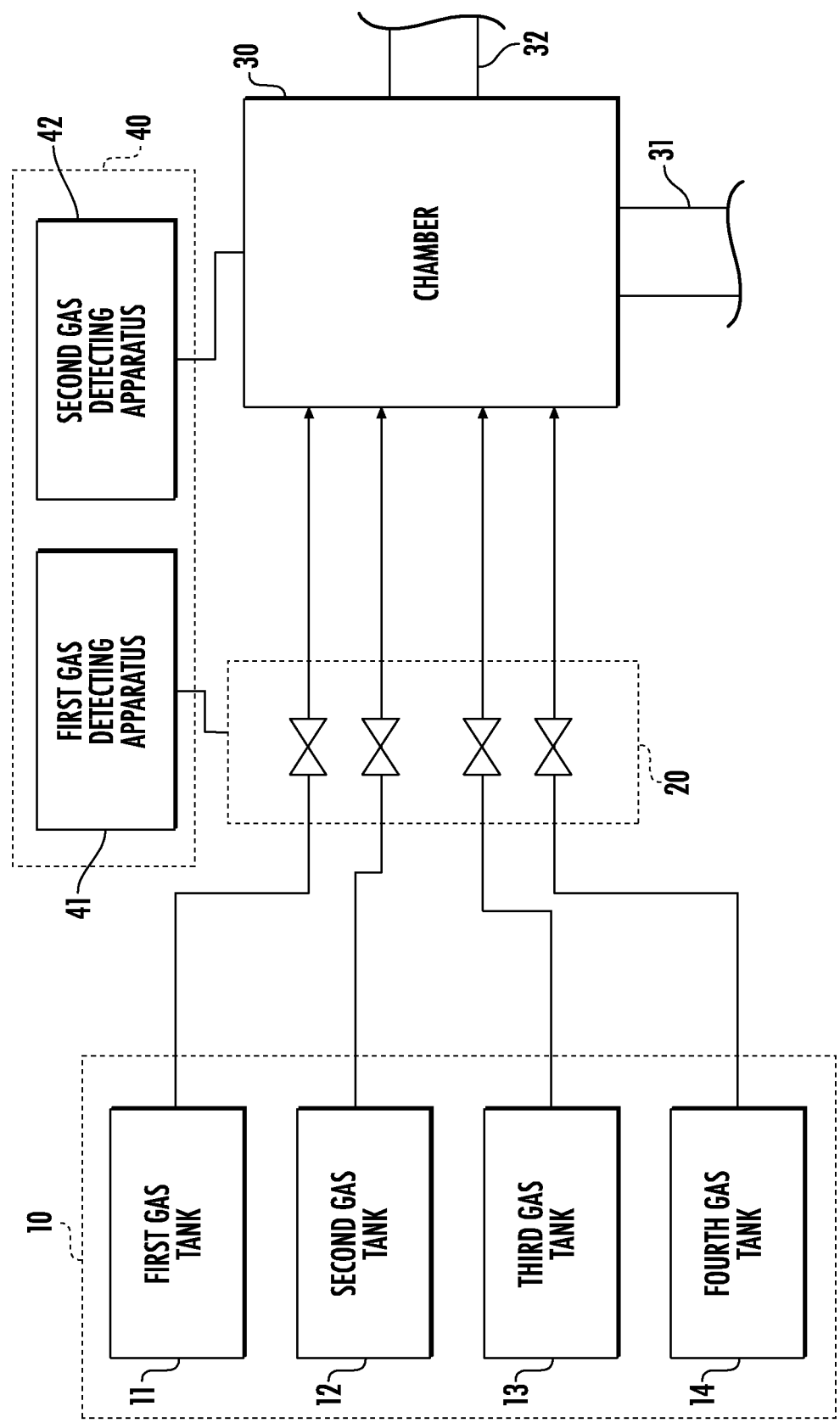
FIG. 1 is a simplified diagram of a processing facility including a gas-detecting apparatus according to one or more embodiments described herein.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The term "comprising" means including but not limited to and should be interpreted in the manner it is typically used in the patent context. Use of broader terms such as "comprises," "includes," and "having" should be understood to provide support for narrower terms such as "consisting of," "consisting essentially of," and "comprised substantially of."

The phrases "in one embodiment," "according to one embodiment," and the like generally mean that the particular feature, structure, or characteristic following the phrase may be included in at least one embodiment of the present disclosure, or may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The "gas-detecting apparatus" as described in the embodiments herein refers to a device for measuring and indicating a concentration of a gas in ambient air. The gas-detecting apparatus has a sensor that aids in measuring the concentration of the gas in the ambient air. The gas-detecting apparatus has one or more audible or visible indicators, such as alarms, lights or a combination of signals to indicate high concentration of the gas. The gas-detecting apparatus can detect one type of gas or more than one type of gases at once. There are different types of gas-detecting apparatuses based on type of sensors used. For example, Electrochemical (EC) sensors, Lower Explosive Limit (LEL) sensors, Nondispersive Infrared (NDIR) sensors, and Photoionization Detector (PID).

The "gas" may either be toxic, flammable or asphyxiant in nature that may be harmful for users working at a site. Presence of the gas above an acceptable level may be undesirable and may lead to a hazardous event. Most common toxic gases include, but are not limited to, carbon monoxide, chlorine, nitrogen oxide and methane. In embodiments described herein, the gas may include a specific gas that is to be detected by the gas-detecting apparatus or varying levels of the specific gas present in external air due to leakage of the specific gas.

Generally, gas-detecting apparatuses are deployed in different work environments to detect leakage of gases that are harmful and toxic and to prevent large scale accidents caused by gas leaks. A gas-detecting apparatus, upon deployment in a work environment, constantly detects gases and when the concentration of the gases exceeds a predetermined value, the gas-detecting apparatus issues an alert for the users. Thereafter, operations at the site may be stalled.

On many instances, due to other factors, such as electrical noise, Radio Frequency (RF) noise, and degradation of a sensor material inside the gas-detecting apparatus, the gas-detecting apparatus may erroneously detect high concentration of a gas and accordingly may raise an alarm. Such alarms may be undesirable.

The apparatuses described herein disclose a gas-detecting apparatus that may detect one or more types of gases in a work environment. In an example embodiment, the gas-detecting apparatus has a gas inlet and a gas outlet, and the gas-detecting apparatus comprises a control module, a sensor module, an air chamber, a valve, a dust filter, a pump, and a solenoid valve.

In an example embodiment, the gas inlet is fluidly coupled to a sensor inlet of the sensor module. The gas inlet is fluidly coupled to a valve outlet of the valve, and the sensor inlet and the valve outlet are fluidly coupled. The sensor module has a sensor outlet that is fluidly coupled to a filter inlet of the dust filter. The dust filter has a filter outlet that is fluidly coupled to a pump inlet of the pump. In an example embodiment, a pump outlet of the pump is fluidly coupled to an inlet of the solenoid valve. The solenoid valve has a first outlet that is coupled to the gas outlet and a second outlet that is fluidly coupled to an air inlet of the air chamber. In an example embodiment, the air chamber has an air outlet that is fluidly coupled to a valve inlet of the valve. In an example embodiment, the inlet, the first outlet and the second outlet of the solenoid valve may be operated by the control module to be opened or closed.

In an example embodiment, the sensor module, the pump, the solenoid valve, and the valve are electrically connected to the control module. In some examples, the control module is configured to control the operation of the sensor module, the pump, the solenoid valve, and the valve.

In an example embodiment, when deployed in the work environment, the gas-detecting apparatus may receive the gas through the gas inlet of the gas-detecting apparatus and the sensor module may receive the gas through the sensor inlet coupled to the gas inlet. The pump then receives the gas through the pump inlet and supplies the gas to the solenoid valve through the pump outlet and the inlet of the solenoid valve. The solenoid valve may then discharge the gas outside the gas-detecting apparatus through the first outlet coupled to the gas outlet.

In an example embodiment, the sensor module continuously detects concentration of the gas received through the sensor inlet. The sensor module then sends a sensing signal to the control module indicative of levels of the concentration of the gas detected at regular intervals. For instance, upon detecting a first level of the concentration of the gas for the first time after deployment, the sensor module may send a first sensing signal to the control module. With an increase in concentration of the gas received by the sensor module, the magnitude of the first sensing signal detected by the sensor module increases accordingly. The control module may have a first threshold value regarding the concentration of the gas above which the gas-detecting apparatus may detect a false alarm event and prevent a false alarm.

After receiving the sensing signal from the sensor module, the control module determines if the magnitude of the sensing signal exceeds the first threshold value. If the control module determines that the magnitude of a first sensing signal is higher than the first threshold value, the control module may open the valve to receive the ambient air from the air chamber to supply the ambient air to the sensor module through the sensor inlet, and close the first outlet of the solenoid valve to stop discharge of the ambient air received from the sensor module. At this point, the sensor inlet receives the gas and the ambient air simultaneously. As the first outlet of the solenoid valve is closed and the second outlet, coupled to the air inlet of the air chamber, is opened, the ambient air and the gas received through the inlet of the solenoid valve is supplied to the air chamber. From the air chamber, the ambient air is then supplied to the sensor module through the valve.

The flow of the ambient air into the sensor module dilutes the concentration of the gas received by the sensor module. The sensor module may detect the concentration of the gas at regular intervals and send corresponding sensing signals to the control module. The sensor module may then detect a second level of the gas and send a second sensing signal related to the second level of the gas to the control module. The control module determines if the magnitude of the second sensing signal is equal or higher than the first threshold value. When the control module determines that the magnitude of the second sensing signal is increasing and is higher than the first threshold value and reaches or exceeds a second threshold value, the control module determines that the second sensing signal rises dues to factors such as RF noise or material degradation and not because of actual rise in concentration of the gas and is a false alarm event. After detecting the false alarm event, the control module may not issue an alarm.

In an example embodiment, if the control module determines that the magnitude of the second sensing signal decreases after the flow of the ambient air into the sensor module and is lower than the first threshold value, the control module determines that the second sensing signal is decreasing due to dilution of the gas with the ambient air and the sensor module is not affected by other factors, such as RF noise and material degradation. In response, the control module issues the alarm.

Thus, the gas-detecting apparatus determines whether or not the level of gas detected is decreased by intaking ambient air. The gas-detecting apparatus has the solenoid valve coupled to the gas outlet of the gas-detecting apparatus, thereby preventing direct exposure of the solenoid valve to the gas and gas adsorption by the solenoid valve. Therefore, the gas-detecting apparatus prevents false alarms due to noise such as an electrical signal or an RF signal and malfunctioning of the gas-detecting apparatus.

The details regarding additional components and functioning of various components of the gas-detecting apparatus is explained further with respect to the figures.

FIG. 1 is a simplified diagram of a processing facility including a gas-detecting apparatus according to an example embodiment of the present inventive concept.

Referring to FIG. 1, a processing facility 1 according to an example embodiment of the present inventive concept may include a gas source 10, a valve 20, a chamber 30, and a gas-detecting apparatus 40. The chamber 30 may receive a gas from the gas source 10 to proceed with a predetermined production process. In some example embodiments, the chamber 30 may be a semiconductor processing apparatus in which a semiconductor process, such as an etching process, a deposition process, a photolithography process, or a cleaning process, is performed. The chamber 30 may be connected to transportation paths 31 and 32 transporting a substrate on which the semiconductor process is performed and may receive gases required for the semiconductor process from the gas source 10.

The gas source 10 may include first to fourth gas tanks 11 to 14 respectively containing different gases. Although the gas source 10 has four gas tanks 11 to 14 in total, in the example embodiment illustrated in FIG. 1, the present inventive concept is not limited thereto. It is obvious that fewer or more gas tanks may be included in the gas source 10. Gases contained in the first to fourth gas tanks 11 to 14 may be supplied to the chamber 30 by operations of the valve 20.

In the example embodiment illustrated in FIG. 1, the gas-detecting apparatus 40 may include a first gas-detecting apparatus 41 and a second gas-detecting apparatus 42. The first gas-detecting apparatus 41 may be connected to the valve 20 to detect whether or not the gas supplied from the first to fourth gas tanks 11 to 14 to the valve 20 has leaked. Meanwhile, the second gas-detecting apparatus 42 may be connected to the chamber 30 to measure a concentration of each of various gases contained in the chamber 30 or to determine whether or not the gas has leaked out of the chamber 30. As necessary, a greater number of gas-detecting apparatuses may be connected to a gas-supplying path, the chamber 30, or the like.

Figure 2:
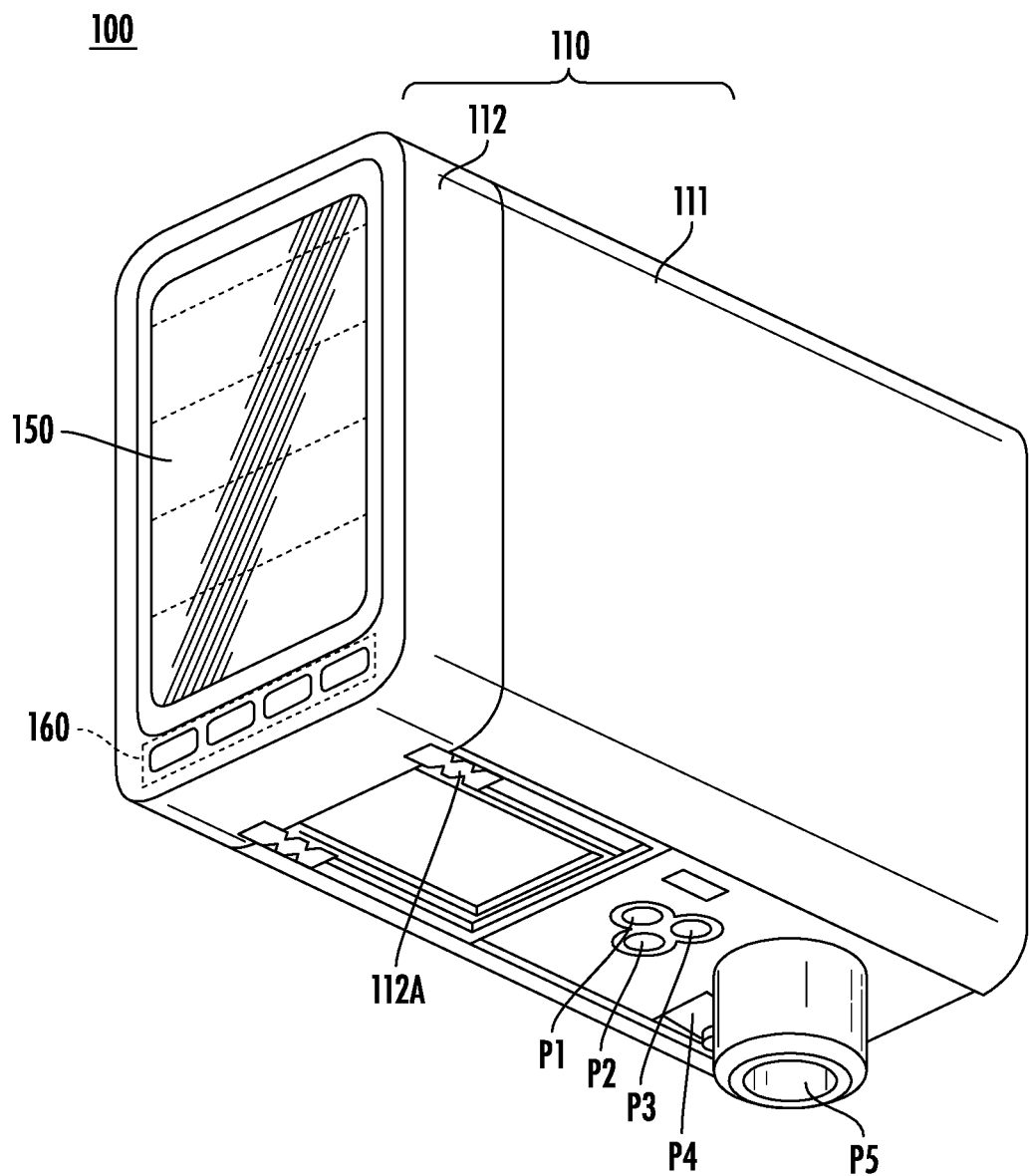
FIGS. 2 and 3 are diagrams illustrating external features of a gas-detecting apparatus according to one or more embodiments described herein.
Figure 3:
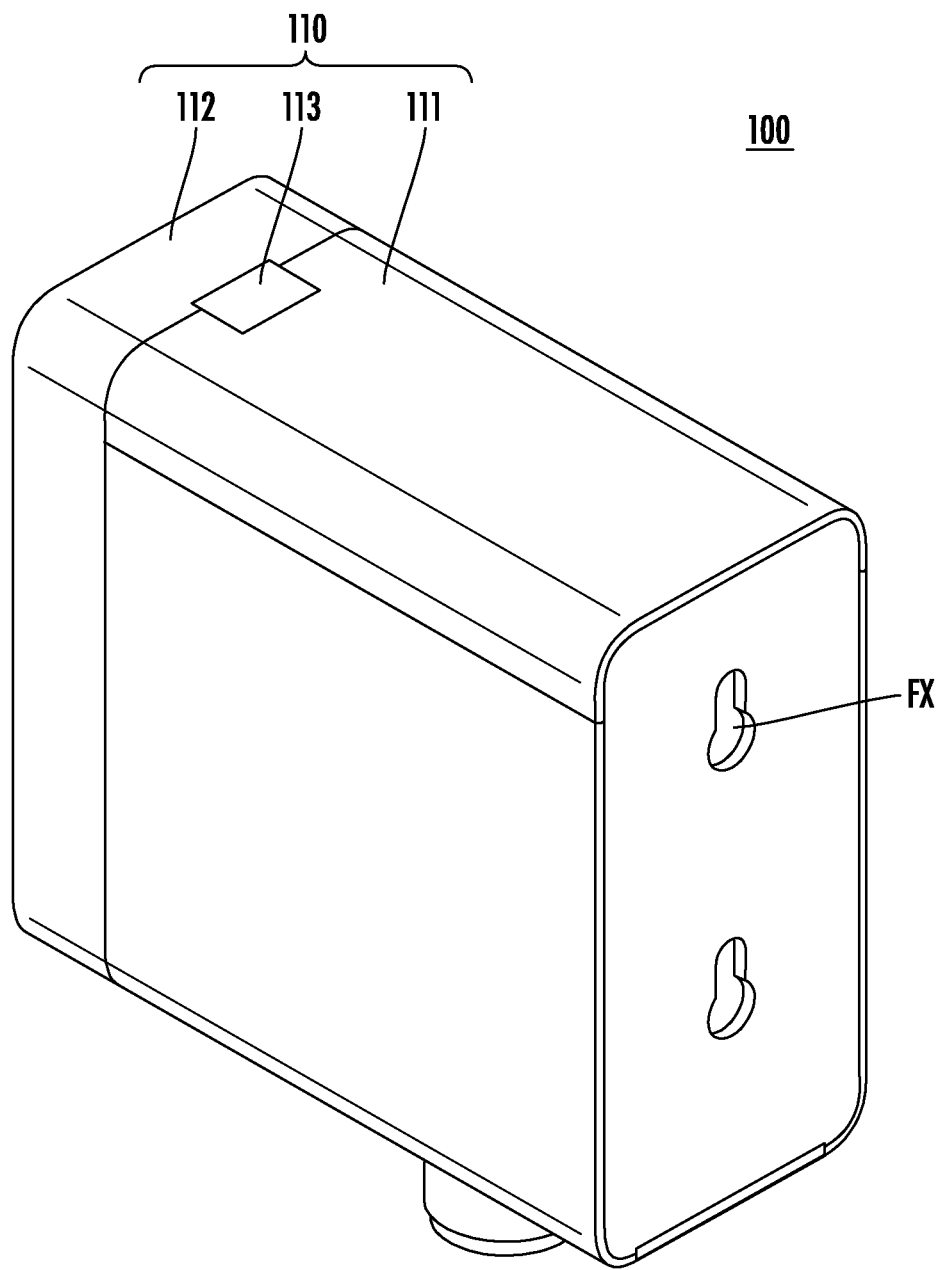

FIGS. 2 and 3 are diagrams illustrating external features of a gas-detecting apparatus according to an example embodiment of the present inventive concept.

First, referring to FIG. 2, a gas-detecting apparatus 100, according to the example embodiment of the present inventive concept, may include a case 110, a display 150, and an input 160. The case 110 may accommodate a pump module that intakes and discharges gas to detect the gas, a sensor module sensing the gas received by the pump module, a control module controlling overall operations of the gas-detecting apparatus 100, a dust filter to remove dust from the gas and the ambient air, and an air chamber to store pure ambient air without traces of the gas.

The case 110 may include a body 111 and a cover 112 combined with the body 111. The cover 112 may be disposed on a front side of the case 110. In some example embodiments, the display 150 and the input 160 may be disposed on the cover 112. The input 160 may include a plurality of mechanical input keys, or a touch screen integrated with the display 150. In some example embodiments, as shown in FIG. 3, the cover 112 may be combined with the body 111 by a hinge 113 disposed on surfaces of the body 111 and the cover 112. The cover 112 may be rotated with respect to the hinge 113 to expose an inside of the body 111.

Referring to FIG. 2, the body 111 and the cover 112 according to the example embodiment of the present inventive concept may be engaged together by an engagement member 112A. The engagement member 112A may be formed on a surface of the cover 112 to combine and engage the body 111 and the cover 112 and prevent the cover 112 from opening while the gas-detecting apparatus 100 is operated.

Meanwhile, a plurality of ports P1 to P5 may be disposed on a lower surface of the case 110. In some example embodiments, the first port P1 and the second port P2 may be intake ports through which the gas is introduced, and the third port P3 may be an exhaust port through which the gas is discharged. In an example embodiment, the gas is introduced through the first port P1 and not through the second port P2. For this, the first port P1 is opened for gas flow and the second port P2 is closed. The gas introduced through the first port P1 by the operations of the pump module may be discharged through the third port P3 via the sensor module installed inside the case 110. The amount of gas introduced through the first port P1 to be discharged through the third port P3 may be determined by the pump module installed inside the case 110.

In some example embodiments, as described above with reference to FIG. 1, the first port P1 may be connected to a space such as the chamber 30 where a gas leak is determined. Accordingly, when a gas leak is suspected, an alarm may not be immediately initiated, in order to verify whether or not gas has actually leaked.

Meanwhile, the fourth port P4 may be a Power-over-Ethernet (PoE) port. The gas-detecting apparatus 100 may communicate with external devices and receive power required to drive itself through the fourth port P4. The fifth port P5 may be a cable gland through which power is supplied from an external device or a signal is inputted from an external controller.

Referring to FIG. 3, the gas-detecting apparatus 100, according to the example embodiment of the present inventive concept, may include a fixing member FX disposed on a rear surface of the case 110. The fixing member FX may include a hole formed to a predetermined depth in the rear surface of the case 110. A user may install a ring or the like protruding outwardly from a wall or a device in a space in which the gas-detecting apparatus 100 is to be installed and fix the gas-detecting apparatus 100 by inserting the ring into the fixing member FX. The gas-detecting apparatus 100 may intake and discharge the gas through the first port P1 and the third port P3 disposed on the lower surface of the case 110, in a state of being fixed by the fixing member FX.

Figure 4:
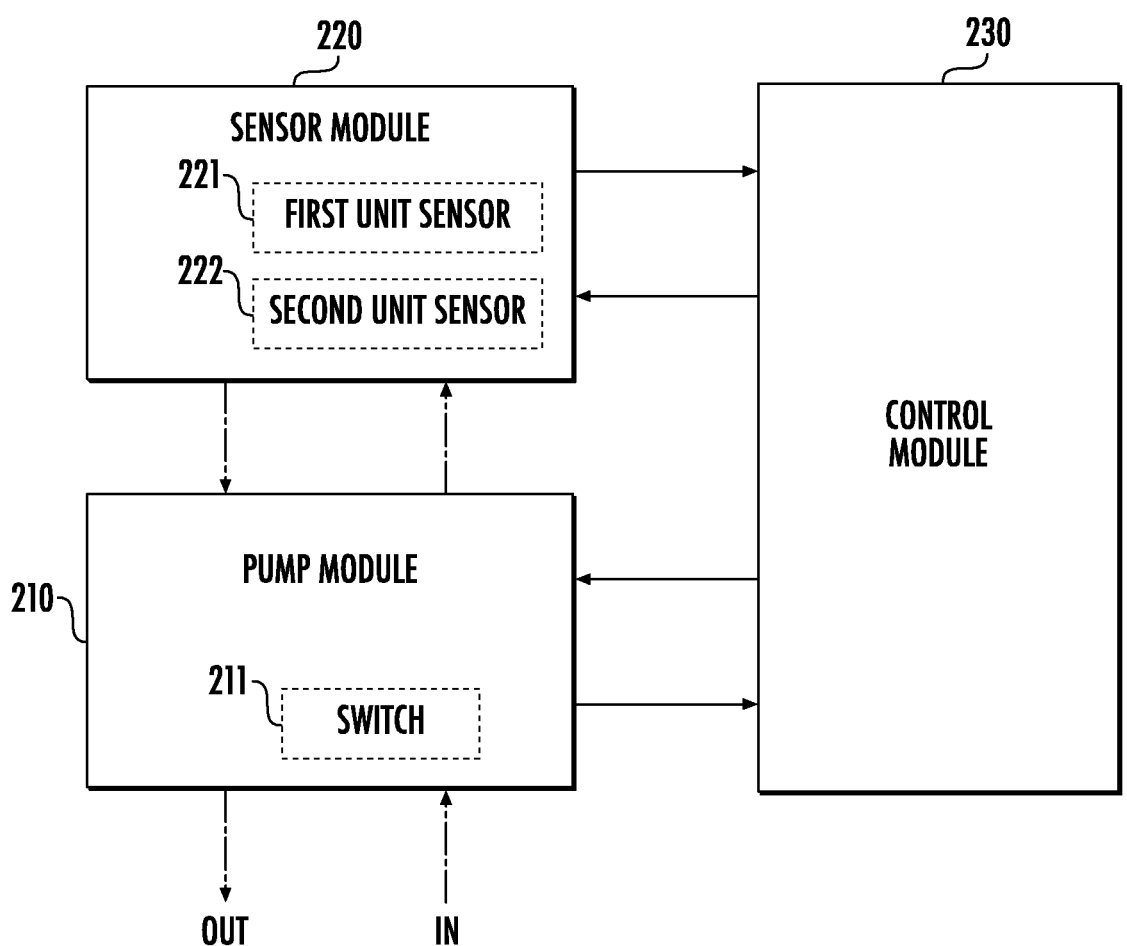
FIG. 4 illustrates a block diagram of the gas-detecting apparatus, according to one or more embodiments described herein.
Figure 5:
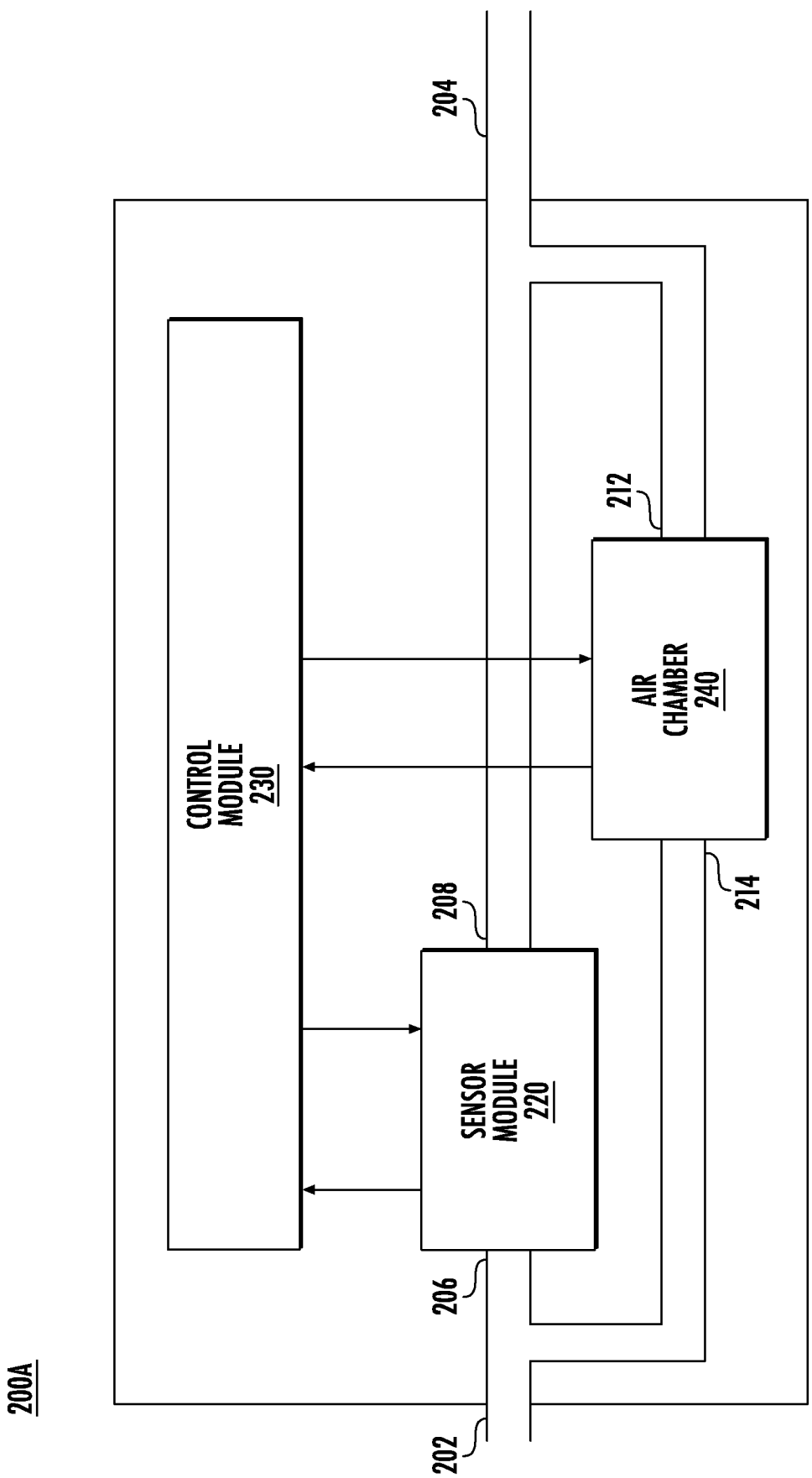
FIGS. 5 and 6 are simplified block diagrams illustrating gas-detecting apparatuses according to one or more embodiments described herein.
Figure 6:
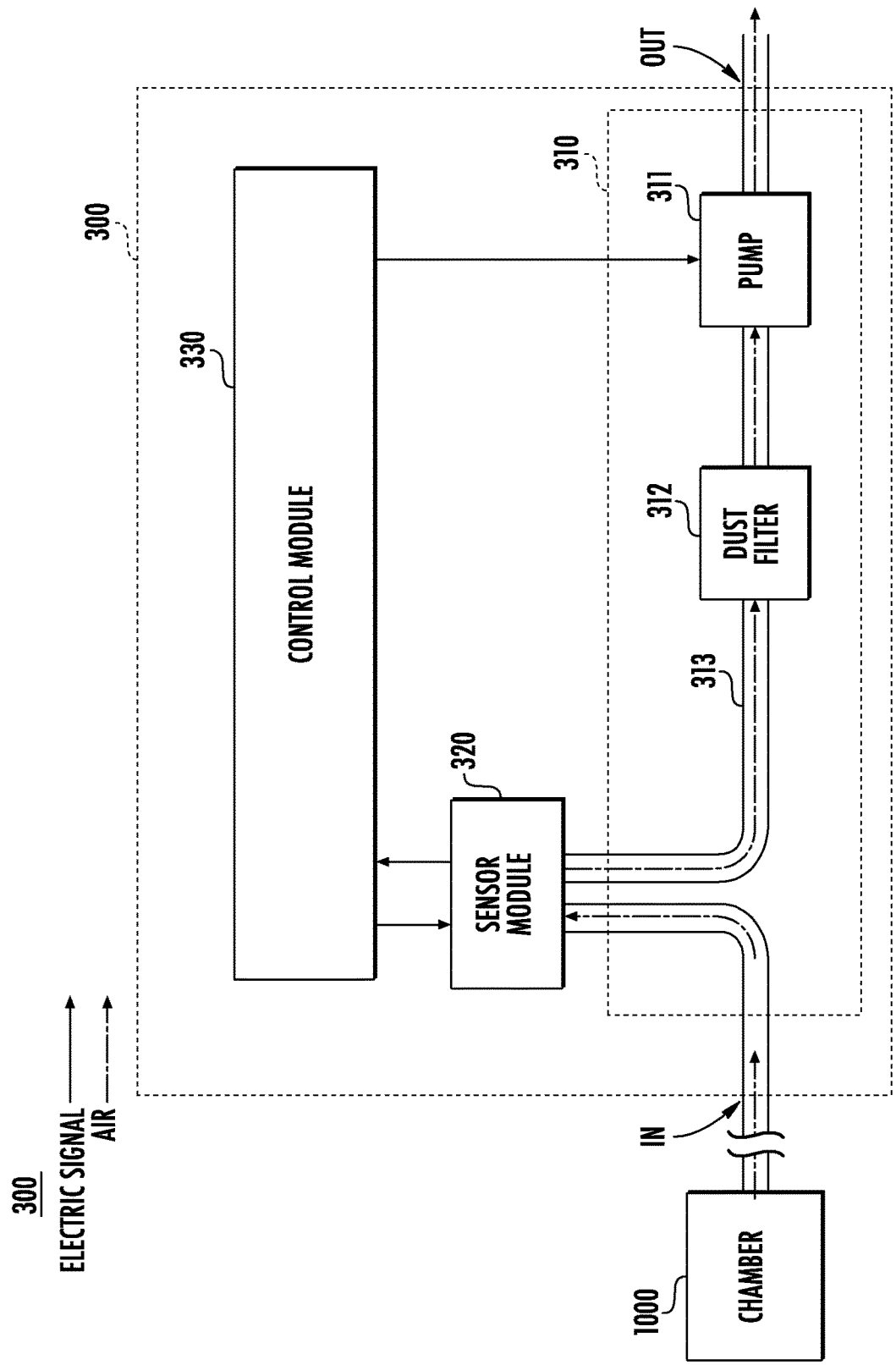

FIGS. 4, 5 and 6 are simplified block diagrams illustrating gas-detecting apparatuses according to example embodiments of the present inventive concept.

Referring to FIG. 4, a gas-detecting apparatus 200, according to an example embodiment described herein, may include a pump module 210, a sensor module 220, and a control module 230. The pump module 210 may include a pump drawing in gas to be supplied to the sensor module 220, a flow rate sensor measuring the amount of the gas received by the pump, and a microtube providing a flow path of the air. The pump module 210 may be connected to ports disposed on a case of the gas-detecting apparatus 200 to intake and discharge the gas. In an embodiment, the pump module 210 may be connected to the ports through a gas inlet to intake the gas and a gas outlet to discharge the gas.

According to the example embodiment of the present inventive concept, the pump module 210 may be connected to an input IN and an output OUT. In some example embodiments, the input IN may be connected to a space in which the gas to be detected is used. The input IN may be connected to a space in which pure ambient air that does not contain the gas to be detected is stored.

The pump module 210 may include a switch 211 selectively opening and closing each of the input IN and the output OUT. In some example embodiments, the switch 211 may be implemented as a solenoid valve, and the control module 230 may control operations of the switch 211. That is, the control module 230 may open and close each of the input IN and the output OUT by controlling the switch 211.

The sensor module 220 may include a plurality of unit sensors 221 and 222 provided to detect gases that the pump module 210 intakes and supplies. Although the sensor module 220 includes the first and second unit sensors 221 and 222 in the example embodiment illustrated in FIG. 4, the number of the unit sensors 221 and 222 included in the sensor module 220 may be variously modified. The unit sensors 221 and 222 may output a sensing signal in response to different kinds of gases.

The control module 230 may supply power to operate the pump module 210 and the sensor module 220 and control the operations of the pump module 210 and the sensor module 220. The control module 230 may include a controller and a power supply circuit. The control module 230 may analyze the sensing signal output by the sensor module 220 to display a type and concentration of a gas present in the space connected to the input IN on a display, or monitor a state of operations of the pump module 210 and the sensor module 220 to display whether or not a failure has occurred on the display.

The control module 230 may output an alarm when a magnitude of the sensing signal output by the sensor module 220 is higher than a threshold value. The alarm may be output on the display or as a specific audio signal. When a gas leak or the like occurs in the space connected to the input IN, a gas concentration may increase regardless of the intention of an operator, resulting in increase in the magnitude of the sensing signal output by the sensor module 220.

When the magnitude of the sensing signal increases and exceeds a first threshold value, the control module 230 may cause an air chamber (not shown) to supply the ambient air to the sensor module 220. When the magnitude of the sensing signal increases while the sensor module 220 intakes ambient air from the air chamber, the control module 230 may determine that the increase in the magnitude of the sensing signal is caused by device failure or noise interference and not due to actual rise of the concentration of the gas. Accordingly, the control module 230 may stop the supply of ambient air from the air chamber, and finally output an alarm when the magnitude of the sensing signal increases to (or above) a second threshold value greater than the first threshold value.

Referring to FIG. 5, a gas-detecting apparatus 200A, according to an example embodiment of the present inventive concept, may include a sensor module 220, a control module 230, and an air chamber 240. In the gas-detecting apparatus 200A according to the example embodiment illustrated in FIG. 5, features of the sensor module 220 and the control module 230 may be similar to those in the gas-detecting apparatus 200 according to the example embodiment illustrated in FIG. 4.

The gas-detecting apparatus 200A has a gas inlet 202 and a gas outlet 204, the sensor module 220 has a sensor inlet 206 and a sensor outlet 208, and the air chamber 240 has an air inlet 212 and an air outlet 214.

In an example embodiment, the gas inlet 202 is fluidly coupled to the first port P1, as shown in FIG. 2, to receive the gas. The gas inlet 202 is fluidly coupled to the sensor inlet 206 of the sensor module 220. In an example embodiment, the gas inlet 202 is coupled to the input IN of the pump module 210 and the sensor inlet 206 is fluidly coupled to the input IN. The gas inlet 202 is fluidly coupled to the air outlet 214 of the air chamber 240, and the sensor inlet 206 and the air outlet 214 are fluidly coupled. The gas outlet 204 is fluidly coupled to the third port P3, as shown in FIG. 2, to discharge the gas out of the gas detecting apparatus 200A. In an example embodiment, the gas outlet 204 is coupled to the output OUT of the pump module 210. In an example embodiment, the gas outlet 204 is fluidly coupled to the sensor outlet 208 and the air inlet 212. Further, the sensor outlet 208 is fluidly coupled to the output OUT.

In an example embodiment, the sensor module 220 and the air chamber 240 are electrically connected to the control module 230. In some examples, the control module 230 is configured to control the operation of the sensor module 220 and the air chamber 240.

In an example embodiment, prior to detecting the gas, the air chamber 240 receives the ambient air from the ambient. The ambient air may be received using the pump module 210 or an external pump connected to the air chamber 240. In an example, the ambient air is received when there is no gas leakage or presence of gas in the ambient air. Thus, the ambient air stored in the air chamber 240 does not include the gas in any concentration.

For detecting the gas, the gas-detecting apparatus 200A may receive the gas through the first port P1 and the gas inlet 202 of the gas-detecting apparatus 200A. In an example embodiment, the sensor module 220 receives the gas through the sensor inlet 206. The sensor module 220 continuously detects concentration of the gas and sends the sensing signal to the control module 230 regarding a concentration of the gas detected. In an example, the sensor module 220 may send a first sensing signal for a first level of gas to the control module 230. The control module 230 may have a first threshold value stored regarding a level of the gas above which an alarm may be raised under normal circumstances. In an example embodiment, the first threshold value may be provided by a user or an operator to be stored in the control module 230.

After receiving the sensing signal from the sensor module 220, the control module 230 determines if the sensing signal indicative of a first level of the gas exceeds the first threshold value. If the control module 230 determines that the first level of gas is higher than the first threshold value, the control module 230 causes the air chamber 240 to supply ambient air to the sensor module 220 through the air outlet 214. In an example embodiment, the air chamber 240 may have a valve opening (not shown) at the air outlet 214 and the control module 230 may open the valve opening to allow flow of the ambient air from the air chamber 240 to the sensor module 220.

The flow of the ambient air into the sensor module 220 along with the flow of the gas dilutes concentration of the gas received by the sensor module 220. The sensor module 220 may then detect a second level of the gas and send a second sensing signal related to the second level of the gas to the control module 230. The control module 230 determines if magnitude of the second sensing signal is equal or higher than the first threshold value. When the control module 230 determines that a magnitude of the second sensing signal is equal or higher than the first threshold value, the control module 230 determines a false alarm event. In an example embodiment, if the magnitude of the second sensing signal rises to or above a second threshold value, the control module 230 determines the false alarm event. Thereafter, the alarm is not issued. In an example embodiment, if the control module 230 determines that the magnitude of the second sensing signal decreases and is lower than the first threshold value, the false alarm event is not detected and, in response, the alarm is issued.

Various components and working of the components are described in detail with reference to FIG. 6, FIG. 7 and FIG. 8.

Figure 7:
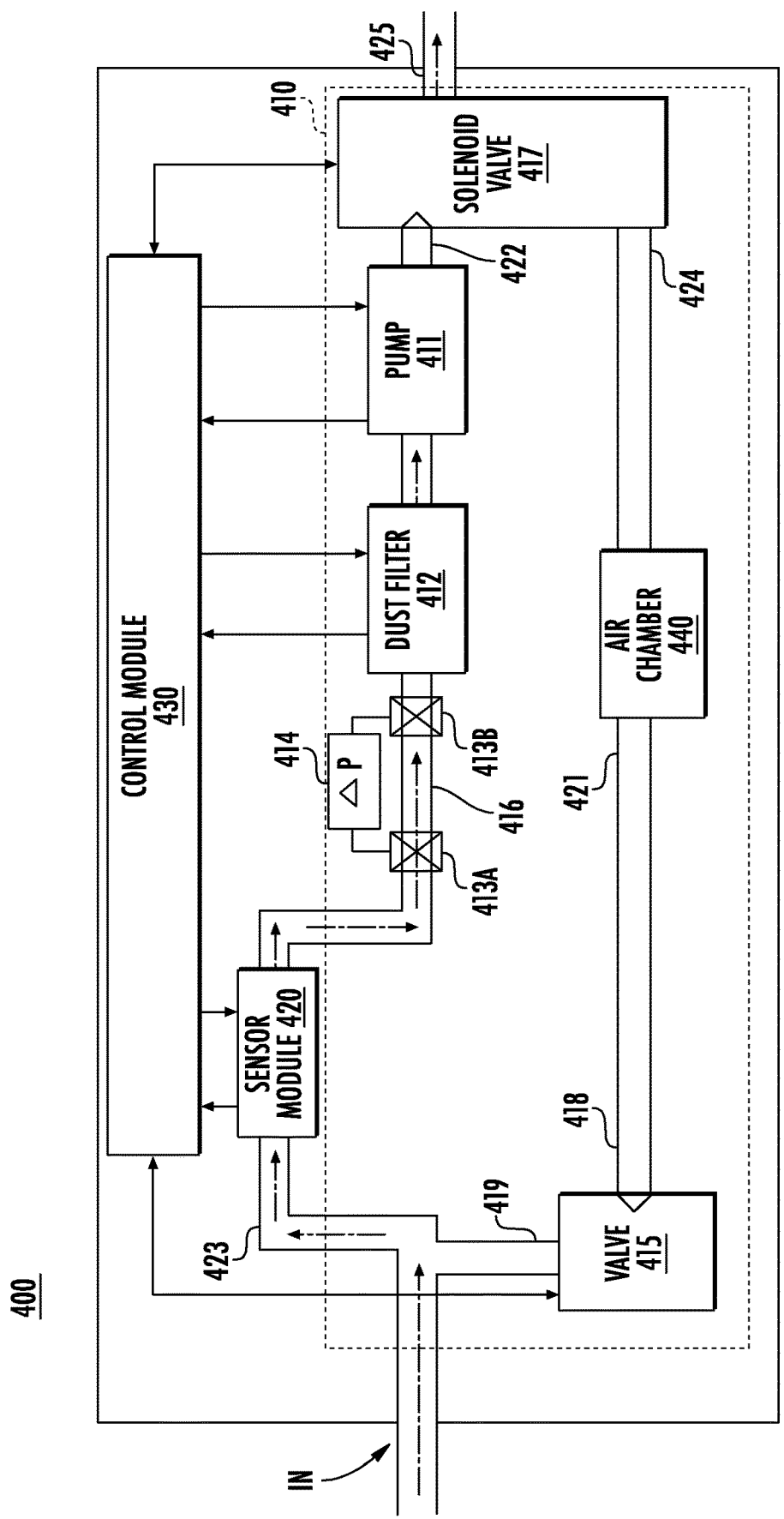
FIGS. 7 and 8 are diagrams provided to illustrate operations of a gas-detecting apparatus according to one or more embodiments described herein.
Figure 8:
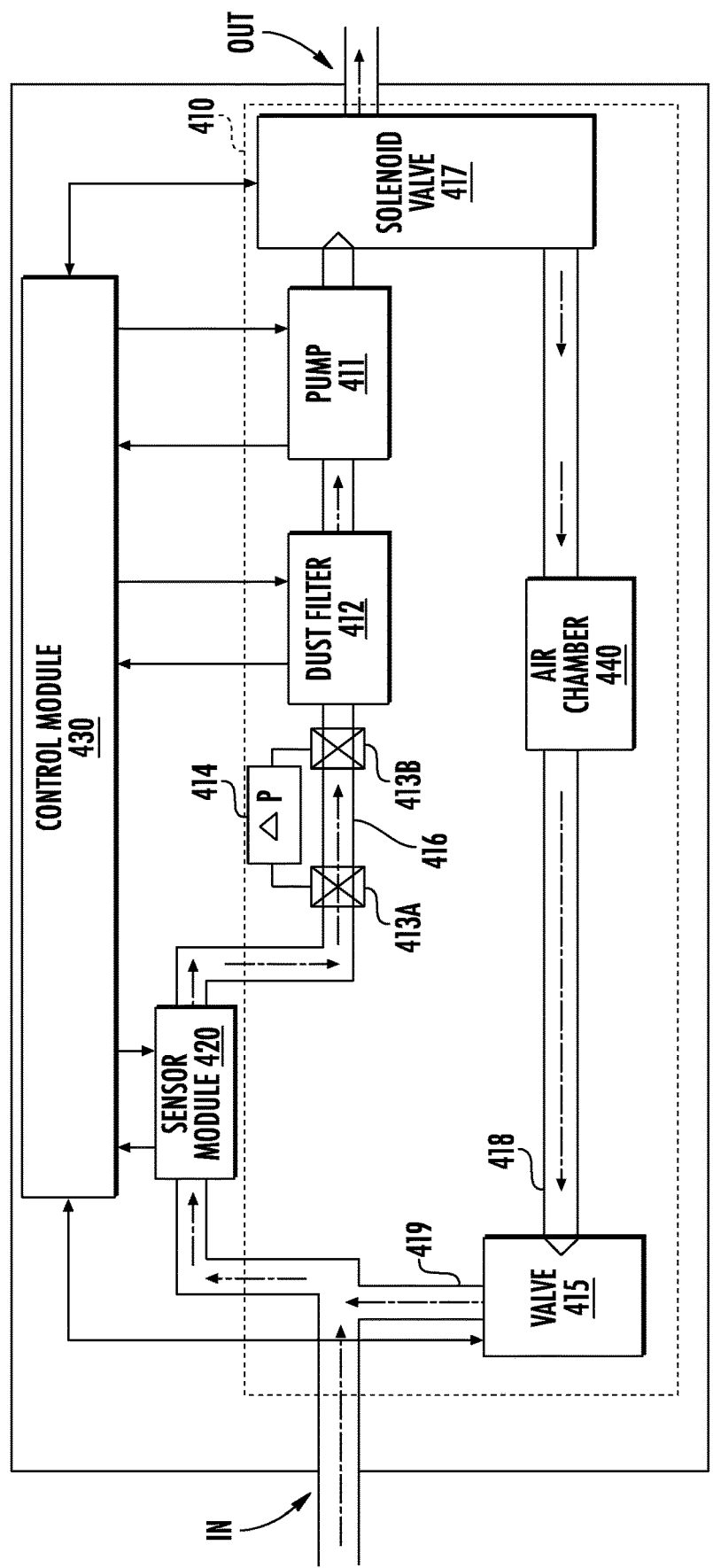

FIGS. 6 to 8 are diagrams provided to illustrate operations of a gas-detecting apparatus according to an example embodiment described herein.

First, FIG. 6 is a diagram illustrating a general gas-detecting apparatus 300. Referring to FIG. 6, the gas-detecting apparatus 300 may include a pump module 310, a sensor module 320, and a control module 330, and an input IN of the pump module 310 may be connected to a chamber 1000 in which a gas leak is monitored. The pump module 310 may supply the gas received through the input IN to the sensor module 320, and the gas passing through the sensor module 320 may be discharged externally through an output OUT.

The pump module 310 may include a pump 311, a dust filter 312, and a microtube 313. The dust filter 312 may remove dust in the gas received by the pump 311 in order to prevent shortening a lifespan of the pump 311 due to foreign substances. The microtube 313 may provide a path through which the air flows in the gas-detecting apparatus 300. Operations of the pump module 310 and the sensor module 320 may be controlled by the control module 330.

In the gas-detecting apparatus 300 illustrated in FIG. 6, the control module 330 may detect a gas leak in the chamber 1000 and output an alarm, using the magnitude of a sensing signal output by the sensor module 320 in response to the gas detected. However, since the gas-detecting apparatus 300 illustrated in FIG. 6 does not have a means for distinguishing the increase in the magnitude of the sensing signal output from sensor module 320 due to a malfunction of the sensor module 320 or an external electrical noise or radio frequency (RF) noise, from the increase in the magnitude of the sensing signal due to the gas leak, a false alarm may be output. Once the alarm is output, an operator may stop the operations of the chamber 1000 or shut off the gas supplied to the chamber 1000 to check whether or not a gas leak has occurred. The output of the false alarm may result in lowering productivity and increasing the personnel and cost for maintenance and management of the chamber 1000 and the gas-detecting apparatus 300.

FIGS. 7 and 8 are diagrams provided to illustrate operations of a gas-detecting apparatus 400 according to an example embodiments, which may solve the problems described above. Referring to FIGS. 7 and 8, the gas-detecting apparatus 400 may include a pump module 410, a sensor module 420, and a control module 430.

The pump module 410 may include a pump 411, a dust filter 412, first and second flow rate sensors 413A and 413B, a pressure computing unit 414, a valve 415, a microtube 416, a solenoid valve 417 and an air chamber 440. The valve 415 may be disposed at an intake portion at which the pump module 410 intakes gas, and the pump module 410 may intake the gas contained in the chamber (not shown) through an input IN, and ambient air contained in the air chamber 440 through the valve 415. For example, the chamber may include a space to be inspected for gas leakage, and the air chamber 440 may include pure ambient air that does not include the gas to be inspected.

The first and second flow rate sensors 413A and 413B and the pressure computing unit 414 may be provided to measure pressure of the gas flowing through the microtube 416. The pressure computing unit 414 may compute the pressure of the gas by calculating a difference between a pressure measured by the first flow rate sensor 413A at a first point of the microtube 416 and a pressure measured by the second flow rate sensor 413B at a second point of the microtube 416. The control module 430 may control the amount of the gas received by the pump module 410 with reference to the pressure difference calculated by the pressure computing unit 414.

First, referring to FIG. 7, the control module 430 may intake the gas contained in the chamber to be supplied to the sensor module 420 by opening the input IN. The gas passing through the sensor module 420 may be discharged to the outside through an output OUT, as shown in FIG. 8. The control module 430 may control the pump module 410 to intake the ambient air contained in the air chamber 440 when the magnitude of the sensing signal output by the sensor module 420 in response to the gas is greater than a first threshold value. The solenoid valve 417 receives the gas through the inlet and discharges the gas through the first output. This will be described in more detail below with reference to FIG. 8.

When the magnitude of the sensing signal output by the sensor module 420 in response to the gas is greater than the first threshold value, the control module 430 may initiate a verification time in which the control module 430 may control the valve 415 to open. As the air chamber 440 is fluidly coupled to the valve 415 through an air outlet 421 and a valve inlet 418, and the valve 415 is fluidly coupled to the sensor module 420 through a valve outlet 419 and a sensor inlet 423, the opening of the valve 415 allows flow of the ambient air into the sensor module 420 from the air chamber 440 through the valve 415. Accordingly, the gas contained in the chamber may be received by the gas-detecting apparatus 400 along with the ambient air stored in the air chamber 440. The control module 430 may open the valve 415 during the verification time, and the sensor module 420 may receive the ambient air along with the gas during the verification time, as illustrated in FIG. 8.

As described above, the air chamber 440 stores the ambient air that does not include the gas. During the verification time, the control module 430 activates the solenoid valve 417 to open an inlet 422, and a second outlet 424, and close a first outlet 425 to circulate the ambient air within the pump module 410. Accordingly, the magnitude of the sensing signal output by the sensor module 420 may decrease during the verification time. When the magnitude of the sensing signal sufficiently decreases during the verification time, the control module 430 may determine that the magnitude of the sensing signal has increased to the first threshold value or more due to a gas leak occurring in the chamber actually, with no other cause such as a noise or a malfunctioning of the sensor module 420. Accordingly, the control module 430 may determine that there is no possibility that a false alarm has occurred.

After the verification time elapses, the control module 430 may close the valve inlet 418 and the valve outlet 419 to stop flow of the ambient air from the air chamber 440 to the sensor module 420. The gas, at this point, remains flowing into the input IN from the chamber. Here, since there is no other cause such as a noise or malfunctioning of the sensor module 420, the magnitude of the sensing signal output by the sensor module 420 may increase again. In some example embodiments, the control module 430 may output an alarm when the magnitude of the sensing signal increases again to (or above) the first threshold value, or to (or above) a second threshold value that is greater than the first threshold value.

That is, the gas-detecting apparatus 400 according to the example embodiment described herein may not output an alarm as soon as the sensing signal output by the sensor module 420 increases. Instead, when the sensing signal increases and exceeds the first threshold value, the gas-detecting apparatus 400 may supply the ambient air that does not include the gas to the sensor module 420 by operating the valve 415 during the predetermined verification time. Unless the sensing signal increases due to another cause such as external noise or malfunctioning of the sensor module 420, the magnitude of the sensing signal may decrease since the air that does not include the gas is supplied to the sensor module 420. Unless the magnitude of the sensing signal decreases during the verification time, the control module 430 may determine that the magnitude of the sensing signal has increased due to other causes such as device failure or noise interference, and the gas-detecting apparatus 400 may output a device maintenance alarm. On the other hand, when the magnitude of the sensing signal decreases during the verification time, the control module 430 may supply air contained in the space in which a gas leak has occurred to the sensor module 420 by operating the valve 415 again, and determine whether to output the alarm by referring to the magnitude of the sensing signal. Accordingly, a false alarm is prevented from being output due to other cause such as a device failure or a noise inflow.

The details of the components of the control module 430 and the working of the components is described with reference to FIG. 9 and FIG. 10.

Figure 9:
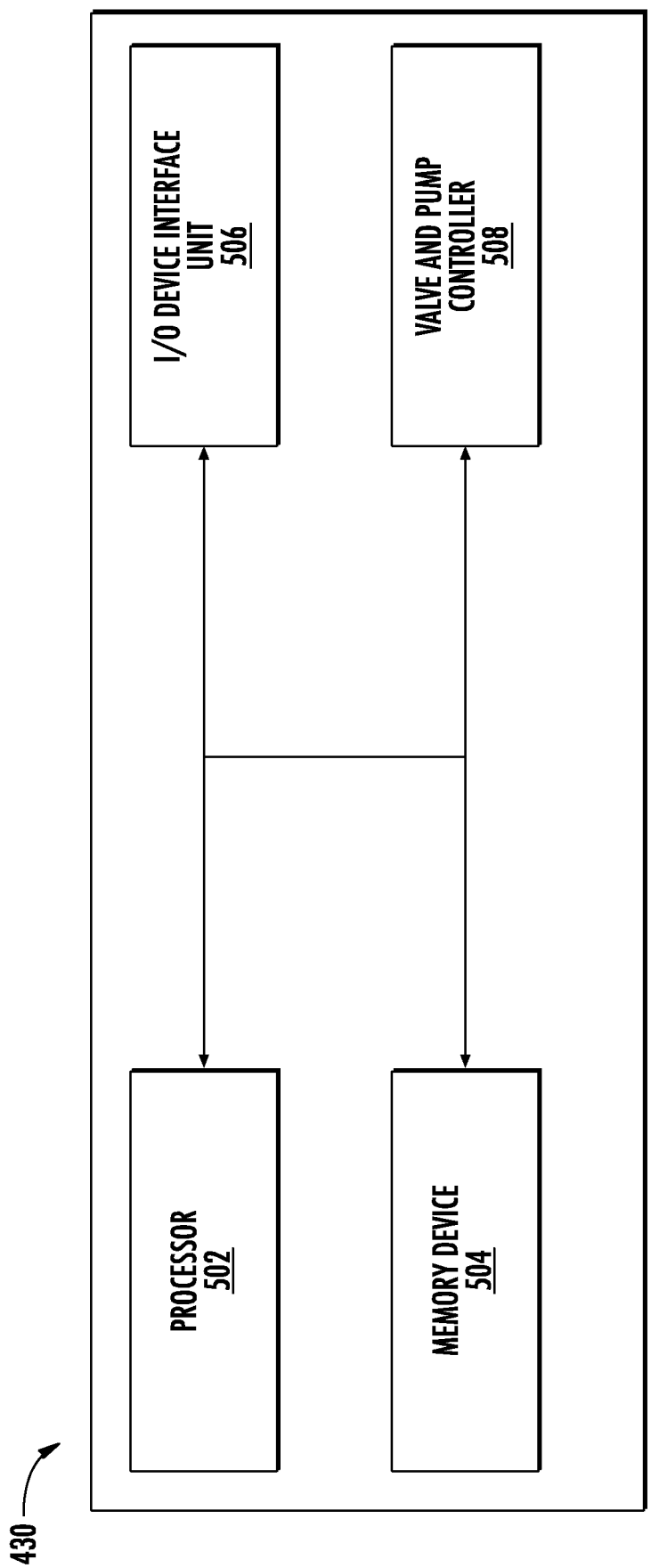
FIG. 9 illustrates a block diagram of components of a control module, according to one or more embodiments described herein.

FIG. 9 illustrates a block diagram of the control module 430, according to one or more embodiments described herein. The control module 430 includes a processor 502, a memory device 504, an input/output (I/O) device interface unit 506, and a valve and pump controller 508.

The processor 502 may be embodied as means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application specific integrated circuit (ASIC) or field programmable gate array (FPGA), or some combination thereof. Accordingly, although illustrated in FIG. 9 as a single processor, in an embodiment, the processor 502 may include a plurality of processors and signal processing modules. The plurality of processors may be embodied on a single electronic device or may be distributed across a plurality of electronic devices collectively configured to function as the circuitry of the control module 430. The plurality of processors may be in operative communication with each other and may be collectively configured to perform one or more functionalities of the circuitry of the control module 430, as described herein. In an example embodiment, the processor 502 may be configured to execute instructions stored in the memory device 504 or otherwise accessible to the processor 502. These instructions, when executed by the processor 502, may cause the circuitry of the control module 430 to perform one or more of the functionalities, as described herein.

Whether configured by hardware, firmware/software methods, or by a combination thereof, the processor 502 may include an entity capable of performing operations according to embodiments of the present disclosure while configured accordingly. Thus, for example, when the processor 502 is embodied as an ASIC, FPGA or the like, the processor 502 may include specifically configured hardware for conducting one or more operations described herein. Alternatively, as another example, when the processor 502 is embodied as an executor of instructions, such as may be stored in the memory device 504, the instructions may specifically configure the processor 502 to perform one or more algorithms and operations described herein.

Thus, the processor 502 used herein may refer to a programmable microprocessor, microcomputer or multiple processor chip or chips that can be configured by software instructions (applications) to perform a variety of functions, including the functions of the various embodiments described above. In some devices, multiple processors may be provided dedicated to wireless communication functions and one processor dedicated to running other applications. Software applications may be stored in the internal memory before they are accessed and loaded into the processors. The processors may include internal memory sufficient to store the application software instructions. In many devices, the internal memory may be a volatile or nonvolatile memory, such as flash memory, or a mixture of both. The memory can also be located internal to another computing resource (e.g., enabling computer readable instructions to be downloaded over the Internet or another wired or wireless connection).

The memory device 504 may include suitable logic, circuitry, and/or interfaces that are adapted to store a set of instructions that is executable by the processor 502 to perform predetermined operations. Some of the commonly known memory implementations include, but are not limited to, a hard disk, random access memory, cache memory, read only memory (ROM), erasable programmable read-only memory (EPROM), electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof. In an example embodiment, the memory device 504 may be integrated with the processor 502 on a single chip, without departing from the scope of the disclosure.

The I/O device interface unit 506 may include suitable logic and/or circuitry that may be configured to communicate with the one or more components of the gas-detecting apparatus 400, in accordance with one or more device communication protocols such as, but not limited to, Inter-Integrated Circuits (I2C) communication protocol, Serial Peripheral Interface (SPI) communication protocol, Serial communication protocol, Control Area Network (CAN) communication protocol, and 1-Wire® communication protocol. In an example embodiment, the I/O device interface unit 506 may communicate with the sensor module 420, the valve 415, the pump 411, and the solenoid valve 417 for facilitating the transmission and reception of the data and signal to and from the control module 430, as is further described in conjunction with FIG. 10. Some examples of the I/O device interface unit 506 may include, but not limited to, a Data Acquisition (DAQ) card, an electrical drives driver circuit, and/or the like.

Figure 10:
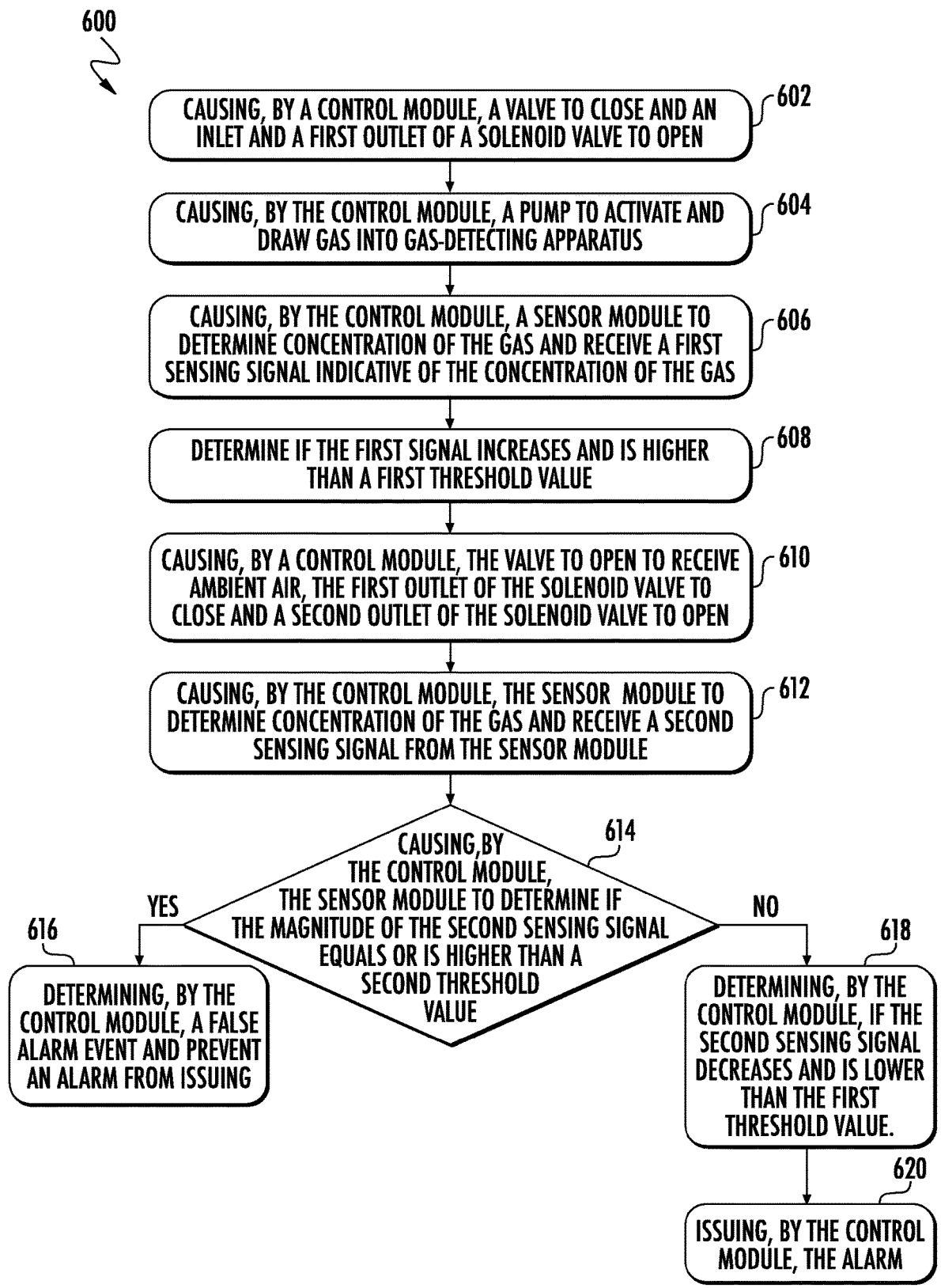
FIG. 10 illustrates a flowchart of a method for preventing a false alarm in gas detection by a gas-detecting apparatus, according to one or more embodiments described herein.

The valve and pump controller 508 may include suitable logic and/or circuitry that may instruct the valve 415, the solenoid valve 417, and the pump 411 to operate and control flow of the gas and the ambient air into the gas-detecting apparatus 400, as is further described in FIG. 10. The valve and pump controller 508 may be further configured to switch states of the valve 415 and the solenoid valve 417 between an open state and a closed state to control flow of the ambient air and the gas in the gas-detecting apparatus 400. The valve and pump controller 508 may be implemented using one or more hardware components, such as, but not limited to, FPGA, ASIC, and the like.

The operation of the control module 430 is described later in conjunction with FIG. 10.

Referring to FIG. 10, in conjunction with FIG. 4, FIG. 5, FIG. 6, FIG. 7, FIG. 8 and FIG. 9, a flowchart 600 illustrating operations for preventing a false alarm in gas detection by a gas-detecting apparatus, such as the gas-detecting apparatus 200, 300 or 400 is described. FIG. 10 shows the flowchart 600 illustrating operation of the control module 430, in accordance with the example embodiments described herein.

Turning first to step 602, the gas-detecting apparatus 400 includes means, such as the control module 430, the processor 502, the valve and pump controller 508, and/or the like, to cause closing of the valve 415 by activating a closed state of the valve 415, and opening the inlet 422 and the first outlet 425 of the solenoid valve 417 by activating the solenoid valve 417. For this, the valve and pump controller 508 is configured to send a signal to the valve 415 for the closed state and the solenoid valve 417 for opening the first outlet 425.

At step 604, the gas-detecting apparatus 400 includes means, such as the control module 430, the processor 502, the valve and pump controller 508, and/or the like, to cause the pump 411 to activate and draw the gas into the gas-detecting apparatus 400 through the gas inlet 202 and the sensor inlet 206. In an example embodiment, the gas may be drawn from a chamber, such as the chamber 1000. When the gas is received into the gas-detecting apparatus 400 through the gas inlet 202 and the sensor inlet 206, the processor 502 causes the sensor module 420 to determine concentration of the gas and receive a corresponding sensing signal, for instance, a first sensing signal, from the sensor module 420, at step 606. In an example, the sensor module 420 sends the sensing signals at regular intervals. For instance, the sensor module 420 may send the sensing signals after every 5 seconds. As the concentration of the gas increases, as determined by the sensor module 420, the magnitude of the sensing signals sent to the processor 502 also increases accordingly.

At step 608, the processor 502 determines if the first sensing signal increases and is higher than a first threshold value. The first threshold value may be provided by a user and stored in the processor 502. In an example embodiment, when the magnitude of the first sensing signal is determined to be higher than the first threshold value, the valve and pump controller 508 is configured to open the valve 415 and the second outlet 424 by activating the valve 415 and the solenoid valve 417 in the open state to receive the ambient air and close the first outlet 425 of the solenoid valve 417 to prevent discharge of the ambient air, at step 610. The sensor module 420 receives the gas and the ambient air from the air chamber 440 through the valve 415.

At step 612, the sensor module 420 determines the concentration of the gas received after receiving the ambient air along with the gas and receives a second sensing signal from the sensor module 420. The processor 502 may determine if the magnitude of the second sensing signal, indicative of the concentration of the gas after receiving the ambient air, increases and reaches or is higher than a second threshold value, at step 614. At step 616, when the processor 502 determines the magnitude of the second sensing signal is higher than the second threshold value, the processor 502 determines a false alarm event and prevents the alarm from issuing.

At step 618, the gas detecting apparatus 400 includes means, such as the control module 430, the processor 502, and/or the like, to determine when the magnitude of the second sensing signal decreases and becomes lower than the first threshold value. The decrease in the magnitude of the second sensing signal may indicate that the dilution of the gas by the ambient air reduces the concentration of the gas, and other factors such as RF noise and material degradation are not affecting the detection of the gas. At step 620, the gas-detecting apparatus 400 includes means, such as the control module 430, the processor 502, the valve and pump controller 508, and/or the like, to activate and issue the alarm.

In an alternative embodiment, after determining that the magnitude of the second sensing signal decreases, the valve and pump controller 508 is configured to cause the valve 415 and the second outlet 424 of the solenoid valve 417 to close by activating the closed states, and to open the first outlet 425 of the solenoid valve 417 to receive the gas and prevent the ambient air flowing into the sensor module 420. In an example embodiment, if the sensing signal, for instance, a third sensing signal, increases and is higher than the second threshold value, the processor 502 issues the alarm.

Figure 11:
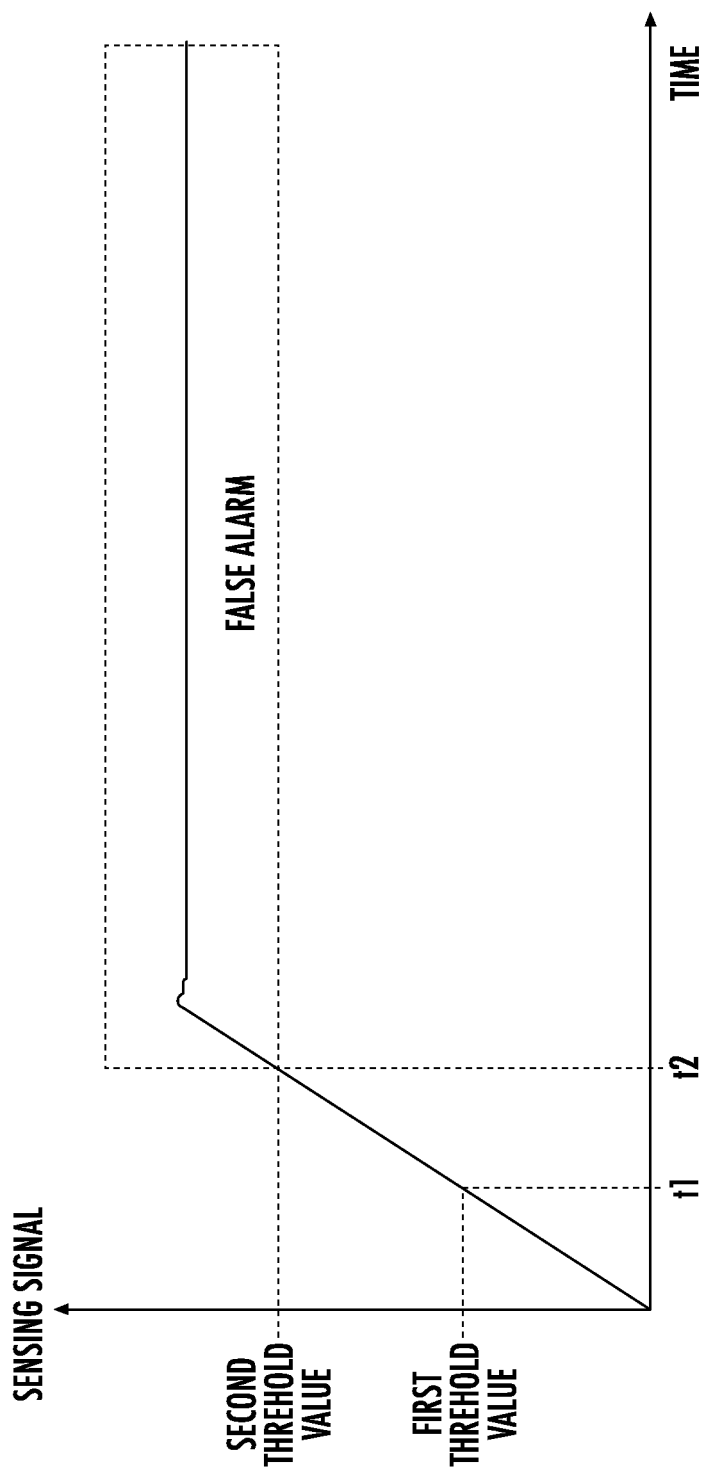
FIGS. 11 and 12 are graphs provided to illustrate operations of a gas-detecting apparatus according to one or more embodiments described herein.
Figure 12:
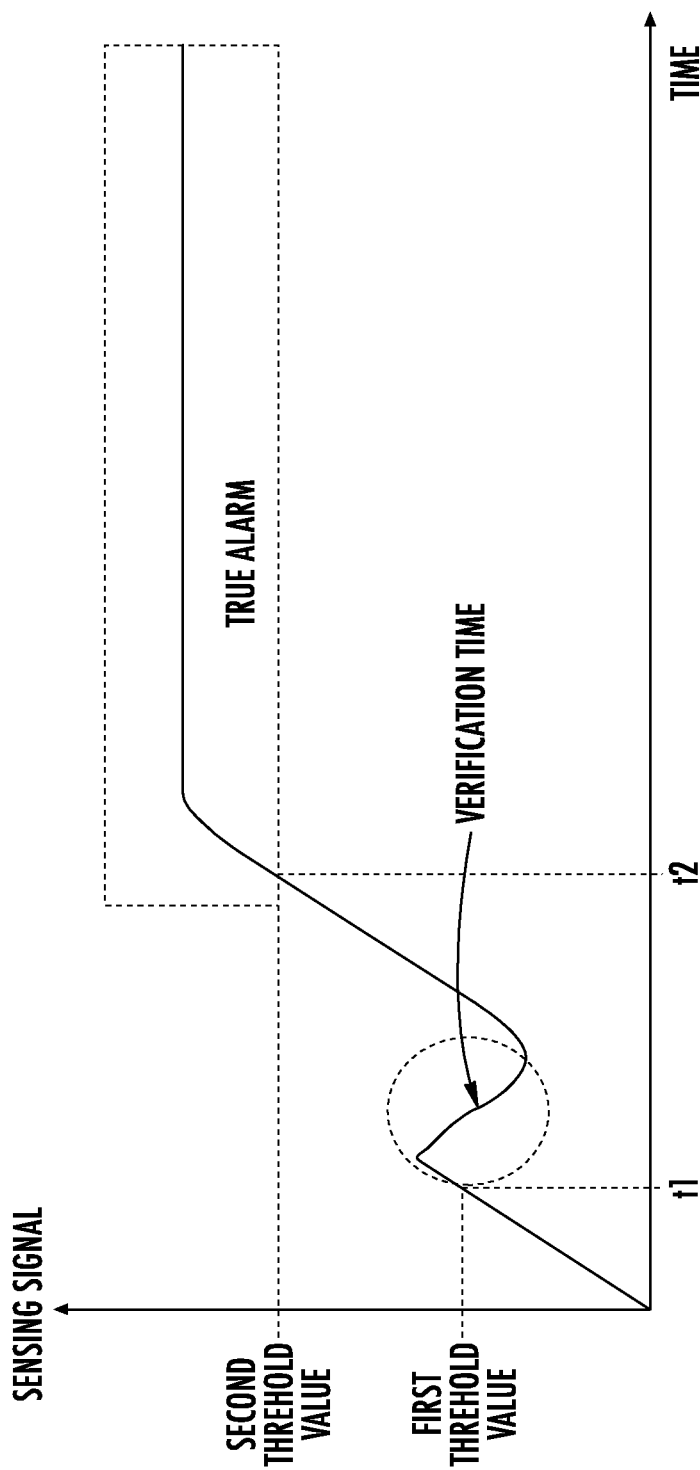

FIGS. 11 and 12 are graphs provided to illustrate operations of a gas-detecting apparatus according to an example embodiment of the present inventive concept.

First, FIG. 11 is a graph provided to illustrate a process of outputting an alarm in a general gas-detecting apparatus. Referring to FIG. 11, the magnitude of a sensing signal output by a sensor module 420 gradually increases to (or above) a first threshold value at a first point in time t1, and to (or above) a second threshold value at a second point in time t2. In the general gas-detecting apparatus, there is no process of verifying whether the increase of the sensing signal occurs due to an actual gas leak or due to an external noise or a malfunction of the sensor module 420. Accordingly, the magnitude of the sensing signal may be simply compared with the first threshold value and the second threshold value sequentially, and the alarm may be outputted when the magnitude of the sensing signal exceeds the second threshold value. However, when the magnitude of the sensing signal increases due to externally introduced electromagnetic noise or a malfunction of the sensor module 420, a false alarm may be outputted.

FIG. 12 is a graph provided to illustrate a process of outputting an alarm in a gas-detecting apparatus according to an example embodiment of the present inventive concept. Referring to FIG. 12, when the magnitude of a sensing signal output by a sensor module 420 gradually increases to (or above) a first threshold value at a first point in time t1, a predetermined verification time may be set. During the verification time, ambient air that does not include the gas may be supplied to the sensor module 420, as described above with reference to FIGS. 7, 8, and 10. Unless there is other cause such as an external noise inflow or a malfunction of the sensor module 420, the ambient air may be supplied to the sensor module 420. Accordingly, the magnitude of the sensing signal may decrease during the verification time, as illustrated in the graph of FIG. 12.

When it is confirmed that the magnitude of the sensing signal decreases during the verification time, the gas to be inspected for gas leakage may be supplied to the sensor module 420 again. Accordingly, the magnitude of the sensing signal may increase again as illustrated in FIG. 10, and the gas-detecting apparatus may output an alarm at a second point in time t2 at which the magnitude of the sensing signal increases to (or above) a second threshold value. According to the example embodiments of the present inventive concept, the air that does not include a gas may be intentionally supplied to the sensor module 420 to check whether or not the magnitude of the sensing signal decreases during the verification time. Accordingly, a gas-detecting apparatus may be implemented to output an alarm only when a gas leak has actually occurred, with no other cause such as an external noise inflow or a malfunction of the sensor module 420.

As set forth above, when a gas leak is suspended due to a sensing signal generated in response to gas, a gas-detecting apparatus according to the example embodiments of the present inventive concept may intake air that does not include the gas for a certain period of time, and may determine whether or not the magnitude of the sensing signal decreases accordingly. Accordingly, a false alarm can be prevented that might be caused due to a malfunction of a sensor, a noise caused by an electric signal or RF signal, or the like. Therefore, smooth operations of a chamber, a gas pipe, or the like connected to the gas-detecting apparatus can be ensured.

While example embodiments have been shown and described above, it will be apparent to those skilled in the art that modifications and variations could be made without departing from the scope of the present invention as defined by the appended claims.

What is claimed is:

1. A gas-detecting apparatus, having a gas inlet and a gas outlet, for detecting a false alarm, the gas-detecting apparatus comprising:
    a control module;
    a sensor module, electrically connected with the control module, the sensor module having a sensor inlet and a sensor outlet, the sensor inlet being fluidly coupled to the gas inlet of the gas-detecting apparatus; and
    an air chamber, having an air inlet and an air outlet, wherein the air inlet is fluidly coupled to the gas outlet of the gas-detecting apparatus and the air outlet is fluidly coupled with the gas inlet of the gas-detecting apparatus;
    wherein the control module is configured to:
        receive a first sensing signal for a first level of gas from the sensor module;
        determine whether a magnitude of the first sensing signal is higher than a first threshold value; and
        cause the air chamber to supply ambient air to the sensor inlet of the sensor module, when the magnitude of the first sensing signal is higher than the first threshold value.

2. The gas-detecting apparatus of claim 1, further comprising a valve electrically connected with the control module, the valve having a valve inlet and a valve outlet, wherein the valve outlet is fluidly coupled to the sensor inlet of the sensor module and the valve inlet is fluidly coupled to the air outlet of the air chamber,
    wherein the control module is configured to cause the valve to:
        open for supplying the ambient air to the sensor inlet, for detection of a false alarm.

3. The gas-detecting apparatus of claim 1, wherein the air chamber stores pure ambient air, the pure ambient air having no traces of the gas.

4. The gas-detecting apparatus of claim 1, wherein the air inlet of the air chamber is configured to receive gas from the sensor outlet of the sensor module.

5. The gas-detecting apparatus of claim 1, wherein the control module is further configured to:
    receive a second sensing signal indicative of a second level of gas in response to supplying the ambient air to the sensor module;
    determine whether a magnitude of the second sensing signal is higher than the first threshold value; and
    determine the false alarm when the magnitude of the second sensing signal is higher than or equal to the first threshold value.

6. The gas-detecting apparatus of claim 5, wherein the control module outputs an alarm when the magnitude of the second sensing signal is lower than the first threshold value.

7. The gas-detecting apparatus of claim 1, further comprising a dust filter having a filter inlet and a filter outlet, the filter inlet of the dust filter being fluidly coupled to the sensor outlet of the sensor module,
    wherein the dust filter is configured to:
        remove dust from one of the ambient air and the gas received from the sensor module.

8. The gas-detecting apparatus of claim 7, further comprising a pressure sensor electrically connected with the control module, wherein the pressure sensor is configured to determine a pressure of one of the gas and ambient air flowing through the sensor outlet of the sensor module to the filter inlet of the dust filter.

9. The gas-detecting apparatus of claim 7, further comprising a pump electrically connected with the control module, wherein the pump has a pump inlet and a pump outlet, the pump inlet being fluidly coupled to the filter outlet of the dust filter.

10. The gas-detecting apparatus of claim 9, further comprising a solenoid valve electrically connected with the control module, the solenoid valve having an inlet, a first outlet and a second outlet, wherein the inlet of the solenoid valve is fluidly coupled to the pump outlet and the second outlet is fluidly coupled to the air inlet of the air chamber, the solenoid valve being configured to:
receive one of the gas and the ambient air through the inlet of the solenoid valve; and
release the gas through the first outlet of the solenoid valve; and
supply the ambient air to the air chamber through the second outlet of the solenoid valve.

11. The gas-detecting apparatus of claim 9, wherein the pump includes an input switch connected to the sensor inlet of the sensor module and an output switch connected to the pump outlet, wherein each of the input switch and the output switch comprises a valve.

12. A gas-detecting apparatus having a gas inlet and a gas outlet, the gas-detecting apparatus comprising:
a control module;
a sensor module electrically connected with the control module, the sensor module having a sensor inlet and a sensor outlet, the sensor inlet being fluidly coupled to the gas inlet of the gas-detecting apparatus;
a valve electrically connected with the control module, the valve having a valve inlet and a valve outlet, wherein the valve outlet is fluidly coupled to the sensor inlet of the sensor module;
an air chamber having an air inlet and an air outlet, wherein the air inlet is fluidly coupled to the gas inlet of the gas-detecting apparatus and the air outlet is fluidly coupled to the gas outlet, wherein the valve inlet is fluidly coupled to the air inlet of the air chamber;
a pump electrically connected with the control module, wherein the pump has a pump inlet and a pump outlet; and
a solenoid valve electrically connected with the control module, the solenoid valve having an inlet, a first outlet, and a second outlet, wherein the inlet of the solenoid valve is fluidly coupled to the pump outlet, and the second outlet is fluidly coupled to the air inlet of the air chamber,
wherein the control module is configured to:
receive a first sensing signal for a first level of gas from the sensor module;
determine whether a magnitude of the first sensing signal is higher than a first threshold value; and
cause the air chamber to supply ambient air to the sensor inlet of the sensor module, when the magnitude of the first sensing signal is higher than the first threshold value.

13. The gas-detecting apparatus of claim 12, wherein the sensor module comprises one or more sensor circuits for detecting the first level of gas.

14. The gas-detecting apparatus of claim 12, wherein the pump includes an input switch connected to the sensor inlet of the sensor module and an output switch connected to the pump outlet.

15. The gas-detecting apparatus of claim 14, wherein each of the input switch and the output switch comprises a valve.

16. The gas-detecting apparatus of claim 12 further comprising a dust filter having a filter inlet and a filter outlet, the filter inlet of the dust filter being fluidly coupled to the sensor outlet of the sensor module, wherein the dust filter is configured to:
remove dust from one of the ambient air and the gas received from the sensor module.

17. The gas-detecting apparatus of claim 16, further comprising a pressure sensor electrically connected with the control module, wherein the pressure sensor is configured to determine a pressure of one of the gas and the ambient air flowing through the sensor outlet of the sensor module to the filter inlet of the dust filter.

18. The gas-detecting apparatus of claim 17, wherein the pressure sensor comprises a first flow rate sensor connected to a first point on a tube, a second flow rate sensor connected to a second point on the tube, and a pressure computing module,
wherein the pressure computing module is configured to:
calculate a pressure of the ambient air and the gas based on values detected by the first flow rate sensor and the second flow rate sensor.

19. The gas-detecting apparatus of claim 18, wherein the sensor outlet of the sensor module is connected with the filter inlet of the dust filter through the tube.

20. A gas-detecting apparatus, having a gas inlet and a gas outlet, for detecting a false alarm, the gas-detecting apparatus comprising:
a control module;
a sensor module, electrically connected with the control module, the sensor module having a sensor inlet and a sensor outlet, the sensor inlet being fluidly coupled to the gas inlet of the gas-detecting apparatus; and
an air chamber, having an air inlet and an air outlet, wherein the air inlet is fluidly coupled to the gas inlet of the gas-detecting apparatus and the air outlet is fluidly coupled with the gas outlet;
wherein the control module is configured to:
receive a first sensing signal for a first level of gas from the sensor module;
determine whether a magnitude of the first sensing signal is higher than a first threshold value; and
cause the air chamber to supply ambient air to the sensor inlet of the sensor module, when the magnitude of the first sensing signal is higher than the first threshold value,
wherein the control module is further configured to:
receive a second sensing signal indicative of a second level of gas in response to supplying the ambient air to the sensor module;
determine whether a magnitude of the second sensing signal is higher than the first threshold value; and
determine the false alarm when the magnitude of the second sensing signal is higher than or equal to the first threshold value.

* * * * *